(12) United States Patent
Nadig

(10) Patent No.: US 12,714,315 B2
(45) Date of Patent: Aug. 25, 2026

(54) WEARABLE DEVICE HAVING A MICRO-ELECTROMECHANICAL SYSTEM (MEMS) RESONATOR FOR SKIN TEMPERATURE SENSING

(71) Applicant: Google LLC, Mountain View, CA (US)

(72) Inventor: Sachin Prakash Nadig, San Francisco, CA (US)

(73) Assignee: GOOGLE LLC, Mountain View, CA (US)

( * ) Notice: Subject to any disclaimer, the term of this patent is extended or adjusted under 35 U.S.C. 154(b) by 683 days.

(21) Appl. No.: 18/187,429

(22) Filed: Mar. 21, 2023

(65) Prior Publication Data

US 2024/0315568 A1 Sep. 26, 2024

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0008* (2013.01); *A61B 5/6801* (2013.01); *G01K 7/32* (2013.01);
(Continued)

(58) Field of Classification Search
CPC ....... A61B 5/0008; A61B 5/01; A61B 5/6801; A61B 2562/0271; A61B 2562/028;
(Continued)

(56) References Cited

U.S. PATENT DOCUMENTS 9,537,466 B1 * 1/2017 Thalmayr .......... H03H 9/02338
9,893,734 B1 * 2/2018 Chillara .................... H03L 7/22
(Continued)

FOREIGN PATENT DOCUMENTS

CN 113702663 A * 11/2021 .......... G01P 15/0975

OTHER PUBLICATIONS

Jha et al., "High Resolution Microresonator-based Digital Temperature Sensor", Applied Physics Letter 91, Aug. 13, 2007, 4 pages (Year: 2007).*
(Continued)

*Primary Examiner* — Aurelie H Tu
*Assistant Examiner* — Andrew E Hoffpauir
(74) *Attorney, Agent, or Firm* — DORITY & MANNING, P.A.

(57) ABSTRACT

A wearable device includes a MEMS resonator. The MEMS resonator is configured to generate an output signal that is indicative of a temperature of a portion of the wearable device that contacts a user's skin when the wearable device is worn by the user. The wearable device includes control circuitry communicatively coupled to the MEMS resonator. The control circuitry is configured to demodulate the output signal and a local oscillator signal indicative of a setpoint temperature for the portion of the wearable device. The control circuitry is configured to determine a phase difference between a phase of the demodulated output signal and a phase of the demodulated local oscillator signal. The control circuitry is further configured to determine a temperature of the user's has changed based on the phase difference.

11 Claims, 8 Drawing Sheets

(51) Int. Cl.
*G01K 7/32* (2006.01)
*G01K 13/20* (2021.01)

(52) U.S. Cl.
CPC ...... *G01K 13/20* (2021.01); *A61B 2562/0271* (2013.01); *A61B 2562/028* (2013.01)

(58) Field of Classification Search
CPC .......... G01K 1/024; G01K 7/32; G01K 13/20; G01K 2211/00
USPC ............................................ 600/549; 331/16
See application file for complete search history.

(56) References Cited

U.S. PATENT DOCUMENTS 10,247,621 B1* 4/2019 Partridge ............. H03K 3/0315
10,622,973 B1 4/2020 Partridge et al.
2005/0151592 A1* 7/2005 Partridge ................ H03L 1/027 331/16
2006/0020312 A1 1/2006 Eggers et al.
2010/0152600 A1* 6/2010 Droitcour ............ A61B 5/7221 600/534
2010/0263445 A1* 10/2010 Hayner .................. G01C 19/56 73/504.12
2010/0308974 A1 12/2010 Rowland et al.
2013/0093525 A1* 4/2013 Le Phan .................. H03B 5/32 331/34
2014/0140364 A1* 5/2014 Charles ................ G01K 15/005 374/178
2016/0038055 A1* 2/2016 Wheeler .............. A61B 5/7225 600/301
2017/0135600 A1* 5/2017 Chien .................. A61B 5/7207
2020/0345971 A1* 11/2020 Schirm ..................... A61F 7/02
2022/0171426 A1 6/2022 Wang et al.
2022/0225929 A1 7/2022 Russell et al.
2023/0248320 A1* 8/2023 Lafon .................... A61B 5/742 600/549
2024/0106436 A1* 3/2024 Hennessy ............... H03L 1/022
2024/0148255 A1* 5/2024 Lee ........................ G01K 7/427

OTHER PUBLICATIONS

CN 113702663 A English Translation (Year: 2021).*

Dr. Steve Arar. 2020. “Analog and Digital Implementation of a Synchronous Demodulator.” Allaboutcircuits.com. All About Circuits. Feb. 13, 2020. https://www.allaboutcircuits.com/technical-articles/analog-and-digital-implementation-of-a-synchronous-demodulator/ (Year: 2020).*

Demir et al., “Fundamental Sensitivity Limitations of Nanomechanical Resonant Sensors Due to Thermomechanical Noise,” in IEEE Sensors Journal, vol. 20, No. 4, pp. 1947-1961, 15 Feb. 15, 2020, doi: 10.1109/JSEN.2019.2948681 (Year: 2020).*

Ruz, et al., 2021. “A Review on Theory and Modelling of Nanomechanical Sensors for Biological Applications” Processes 9, No. 1: 164. https://doi.org/10.3390/pr9010164 (Year: 2021).*

Pandiyan, et al., “Sensitivity improvement of resonant sensor with PID controller,” Proceedings of the 2014 IEEE Students' Technology Symposium, Kharagpur, India, 2014, pp. 170-175, doi: 10.1109/TechSym.2014.6808041 (Year: 2014).*

International Search Report and Written Opinion for Application No. PCT/US2023/081358, mailed Apr. 3, 2024, 13 pages.

International Preliminary Report on Patentability for Application No. PCT/US2023/081358, mailed Oct. 2, 2025. 7 pages.

* cited by examiner

WEARABLE DEVICE HAVING A MICRO-ELECTROMECHANICAL SYSTEM (MEMS) RESONATOR FOR SKIN TEMPERATURE SENSING

FIELD

The present disclosure relates generally to a wearable device having a MEMS resonator configured to sense a temperature of a surface of a housing of the wearable device that comes in contact with the skin of a user wearing the wearable device.

BACKGROUND

Wearable devices can include one or more sensors configured to obtain biometric data (e.g., heart rate, etc.). More specifically, some wearable devices can include a resistor temperature detector (RTD) configured for temperature sensing. In this manner, a wearable device having an RTD can estimate a body temperature of a user wearing the wearable device.

SUMMARY

Aspects and advantages of embodiments of the present disclosure will be set forth in part in the following description, or can be learned from the description, or can be learned through practice of the embodiments.

In one aspect, a wearable device is provided. The wearable device includes a MEMS resonator. The MEMS resonator is configured to generate an output signal that is indicative of a temperature of a portion of the wearable device that contacts a user's skin when the wearable device is worn by the user. The wearable device includes control circuitry communicatively coupled to the MEMS resonator. The control circuitry is configured to demodulate the output signal and a local oscillator signal indicative of a setpoint temperature for the portion of the wearable device. The control circuitry is configured to determine a phase difference between a phase of the demodulated output signal and a phase of the demodulated local oscillator signal. The control circuitry is further configured to determine a temperature of the user's skin has changed based on the phase difference.

In another aspect, a method for determining skin temperature of a user wearing a wearable device having a MEMS resonator and control circuitry communicatively coupled to the MEMS resonator. The method includes obtaining, at the control circuitry, an output signal from the MEMS resonator and indicative of a temperature of a portion of the wearable device that contacts a user's skin when the wearable device is worn by the user. The method includes demodulating, at the control circuitry, the output signal and a local oscillator signal generated by the control circuitry and indicative of a setpoint temperature for the portion of the wearable device. The method includes determining, at the control circuitry, a phase difference between a phase of the demodulated output signal and a phase of the demodulated local oscillator signal. The method includes determining, at the control circuitry, a temperature of the user's skin has changed based on the phase difference.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1:
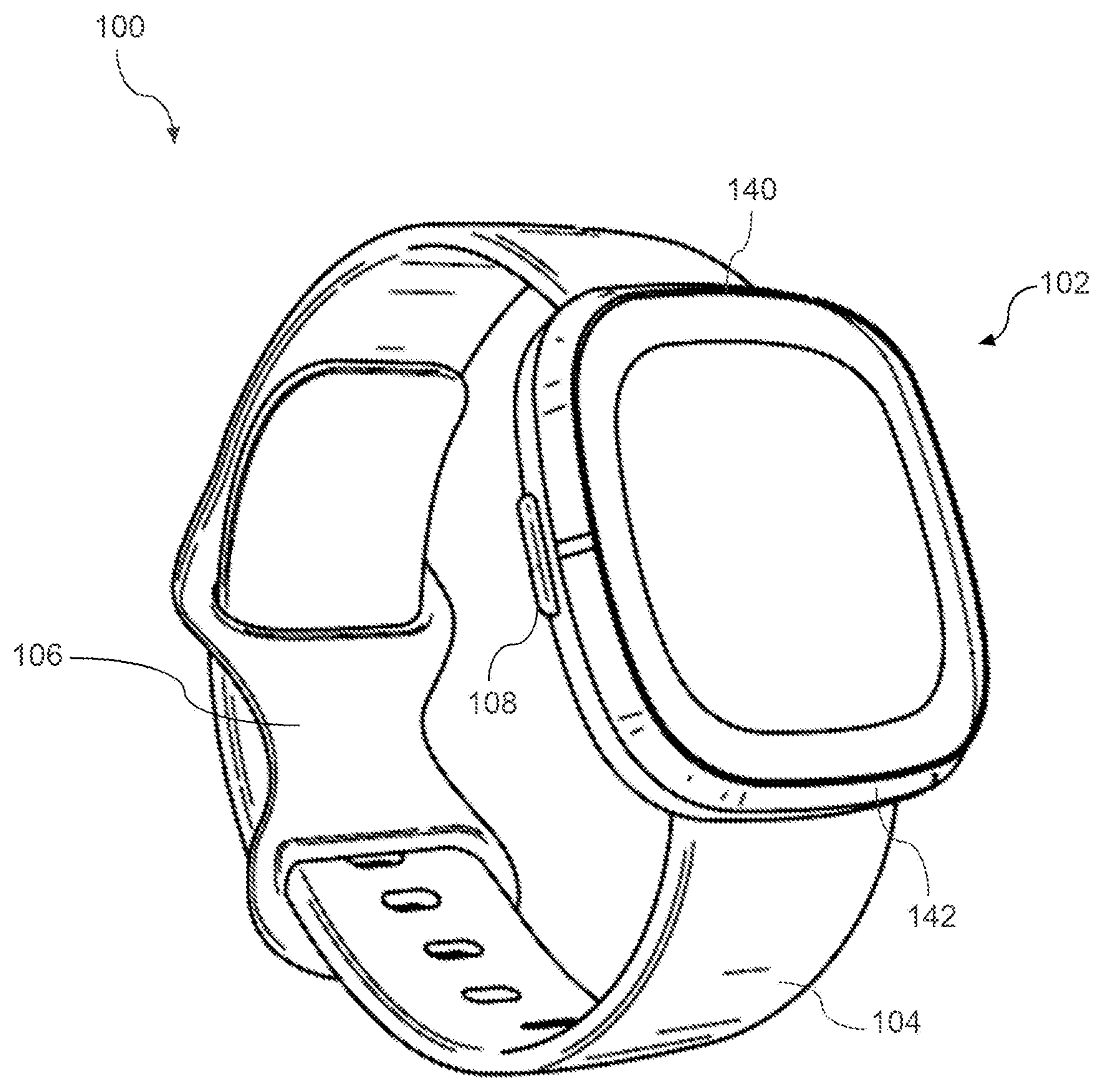
FIG. 1 illustrates a front perspective view of an example, non-limiting wearable device according to one or more example embodiments of the present disclosure.

Reference numerals that are repeated across plural figures are intended to identify the same features in various implementations.

DETAILED DESCRIPTION

Overview

Example aspects of the present disclosure are directed to wearable devices. Some conventional wearable devices can include a resistor temperature detector (RTD) configured for temperature sensing. Alternatively conventional wearable devices can include materials (e.g., platinum wires) for temperature sensing. However, these solutions (e.g., RTD, platinum wires) can be difficult to integrate with a housing of wearable devices. For example, these solutions can require part-to-part calibration and/or polynomial fits to provide accurate temperature sensing (e.g., less than 1° C.). Additionally, these solutions can increase computing requirements and power requirements of wearable devices.

Example aspects of the present disclosure are directed to a wearable device having a MEMS resonator for temperature sensing (e.g., skin temperature). The MEMS resonator can be configured to generate an output signal indicative of a temperature of a portion of a the wearable device that contacts a user's skin when the wearable device is worn by the user. For instance, in some implementations, the MEMS resonator can be coupled to the portion (e.g., wrist-facing side) of the wearable device. In alternative implementations, the MEMS resonator can be integrally formed with the portion of the wearable device.

The wearable device can include control circuitry communicatively coupled to the MEMS resonator. In this manner, the control circuitry can receive the output signal from the MEMS resonator. Furthermore, the control circuitry can include a local oscillator configured to generate a local oscillator signal indicative of a setpoint temperature for the portion of the wearable device.

The control circuitry can include a demodulator. The demodulator can be configured to demodulate the output signal and a local oscillator signal generated by a local oscillator source of the control circuitry and indicative of a setpoint temperature for the portion of the wearable device that contacts the user's skin when the wearable device is worn by the user. The control circuitry can determine a phase difference between a phase of the demodulated output signal and the demodulated local oscillator signal. Furthermore, the control circuitry can determine the temperature of the portion of the wearable device has changed when the phase difference between the demodulated output signal and the demodulated local oscillator signal is non-zero. Furthermore, the control circuitry can determine a temperature of the user's skin has changed based, at least in part, on the phase difference being non-zero.

In some implementations, the control circuitry can be configured to adjust the local oscillator signal output by the local oscillator to eliminate the phase difference. In this manner, the setpoint temperature of the control circuitry can become the newly determined temperature of the portion of the wearable device and the control circuitry can therefore be ready to detect another change (e.g., increase or decrease) to the temperature of the portion of the wearable device that is also indicative of a change to the temperature of the user's skin.

Example aspects of the present disclosure provide numerous technical effects. For instance, the MEMS resonator can be more easily integrated with wearable devices compared to RTDs. For instance, in some implementations, the MEMS resonator can be integrally formed with a portion of the wearable device that contacts the user's skin when the wearable device is worn by the user. Additionally, the output signal of the MEMS resonator can be used by computing device of the wearable device as a clocking signal. In this manner, wearable devices can have less components since the MEMS resonator can operate as both a temperature sensor and a clock source.

With reference now to the Figures, example embodiments of the present disclosure will be discussed in further detail.

Example Devices and Systems

In one or more embodiments, the computing device described above and below according to example embodiments of the present disclosure can constitute, include, be coupled to, and/or otherwise be associated with one or more computing devices and/or computing systems described below and illustrated in the example embodiments depicted in FIGS. 1, 2, 3, 4, 5, and/or 6. For example, in at least one embodiment, the computing device described above and below according to example embodiments of the present disclosure can constitute, include, be coupled to, and/or otherwise be associated with wearable device 100, 100*a*, 100*b*, and/or 100*c*, external computing device 504, 504*a*, 504*b*, and/or 504*c*, and/or server system 604.

Figure 2:
FIG. 2 illustrates a rear perspective view of an example, non-limiting wearable device according to one or more example embodiments of the present disclosure.
Figure 2:
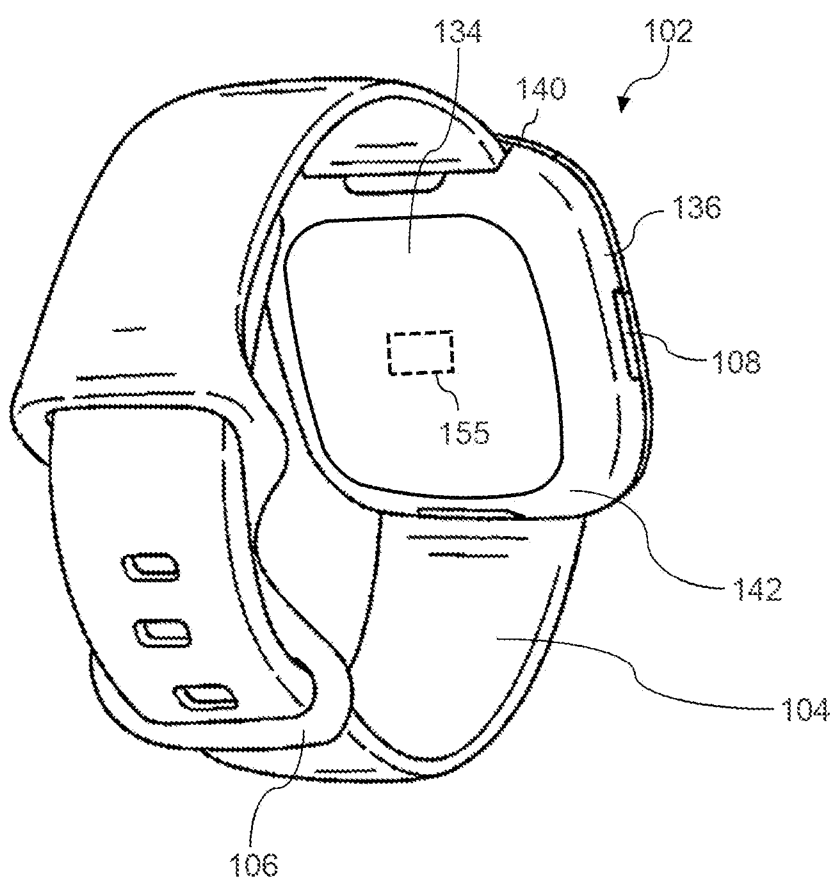
Figure 3:
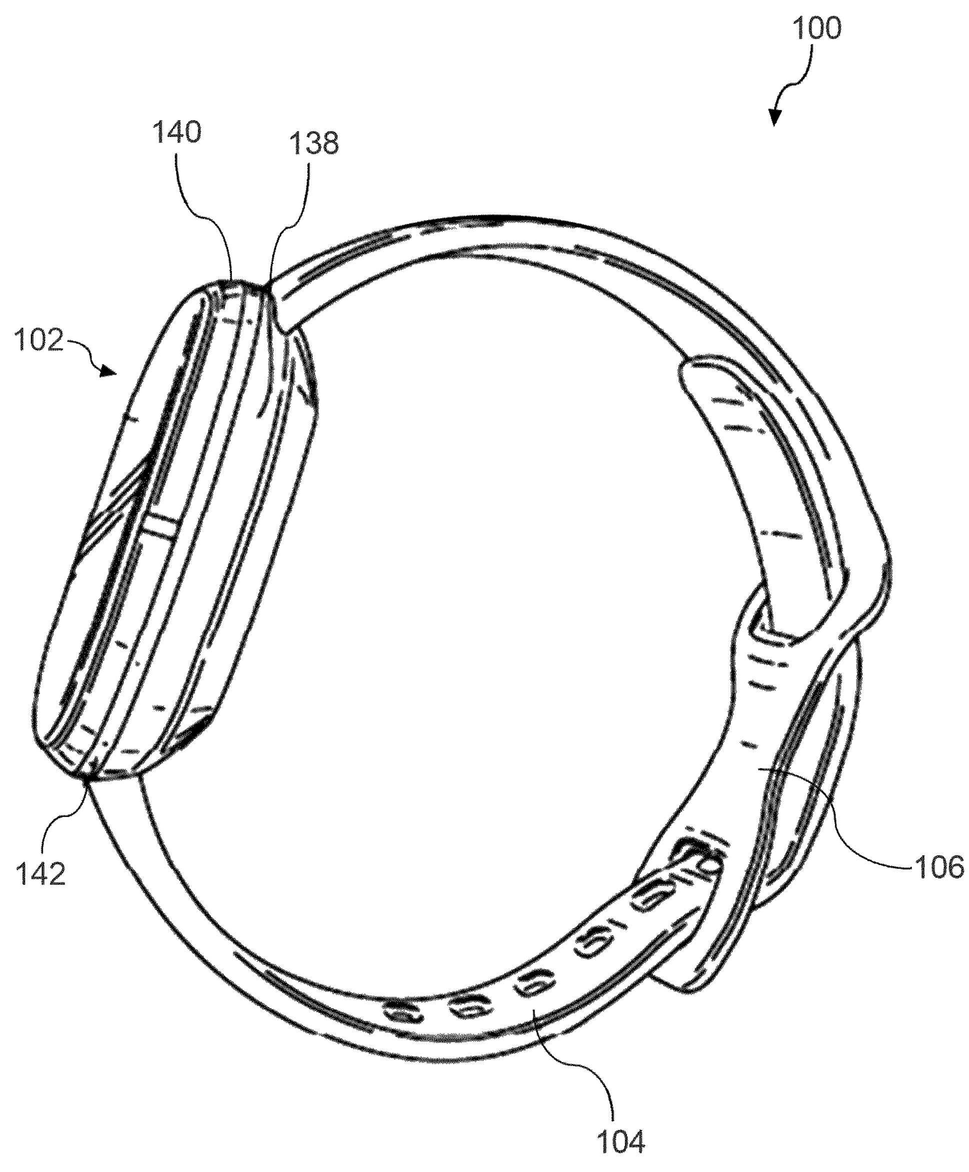
FIG. 3 depicts a side view of an example, non-limiting wearable device according to one or more example embodiments of the present disclosure.

FIGS. 1, 2, and 3 each illustrate a perspective view of an example, non-limiting wearable device 100 according to one or more example embodiments of the present disclosure. In example embodiments described herein, wearable device 100 can constitute and/or include a wearable device. For instance, in these or other example embodiments, wearable device 100 can constitute and/or include a wearable device such as, for example, a wearable physiological monitoring device that can be worn by a user (also referred to herein as a "wearer") and/or capture one or more types of physiological data of the user (e.g., heart rate (HR) data, motion data (e.g., accelerometer data), body temperature data, respiration rate data, blood pressure data, blood oxygenation level data, deoxyribonucleic acid (DNA) data, electrodermal activity (EDA) data, stress related data).

Wearable device 100 according to example embodiments of the present disclosure can include a display 102, an attachment component 104, a securement component 106, and a button 108 that can be located on a side of wearable device 100. In at least one embodiment, two sides of display 102 can be coupled (e.g., mechanically, operatively) to attachment component 104. In some embodiments, securement component 106 can be located on, coupled to (e.g., mechanically, operatively), and/or integrated with attachment component 104. In these or other embodiments, securement component 106 can be positioned opposite display 102 on an opposing end of attachment component 104. In some embodiments, button 108 can be located on a side of wearable device 100, underneath display 102.

Display 102 according to example embodiments described herein can constitute and/or include any type of electronic display or screen known in the art. For example, in some embodiments, display 102 can constitute and/or include a liquid crystal display (LCD) or organic light emitting diode (OLED) display such as, for instance, a transmissive LCD display or a transmissive OLED display. Display 102 according to example embodiments can be configured to provide brightness, contrast, and/or color saturation features according to display settings that can be maintained by control circuitry and/or other internal components and/or circuitry of wearable device 100. In some embodiments, display 102 can constitute and/or include a touchscreen such as, for instance, a capacitive touchscreen. For example, in these embodiments, display 102 can constitute and/or include a surface capacitive touchscreen or a projective capacitive touch screen that can be configured to respond to contact with electrical charge-holding members or tools, such as a human finger.

In some embodiments, display 102 can be configured to provide (e.g., render) a variety of information such as, for example, the time, the date, body signals (e.g., physiological data of a user wearing wearable device 100), readings based upon user input, and/or other information. In one embodiment, such body signals can include, but are not limited to, heart rate data (e.g., heart beats per minute), motion data (e.g., movement data, accelerometer data), blood pressure data, body temperature data, respiration rate data, blood oxygenation level data, deoxyribonucleic acid (DNA) data, electrodermal activity (EDA) data, stress related data and/or any other body signal that one of ordinary skill in the art would understand that can be measured by a wearable device such as, for instance, wearable device 100. In some embodiments, the readings based upon user input can include, but are not limited to, the number of steps a user has taken, the distance traveled by the user, the sleep schedule of the user, travel routes of the user, elevation climbed by the user, and/or any other metric that one of ordinary skill in the art would understand that can be input by a user into a wearable device such as, for instance, wearable device 100.

In at least one embodiment of the present disclosure, the above-described body signals and/or readings based upon user input can be used to calculate further analytics to provide a user with data such as, for instance, a fitness score, a sleep quality score, a number of calories burned by the user, and/or other data. In some embodiments, wearable device 100 can take in (e.g., capture, collect, receive, measure) outside data irrespective of the user such as, for example: an ambient temperature of an environment surrounding and/or external to wearable device 100; an amount of sun exposure wearable device 100 is subjected to; an atmospheric pressure of the environment surrounding and/or external to wearable device 100; an air quality of the environment surrounding and/or external to wearable device 100; the location of wearable device 100 based on, for instance, a global positioning system (GPS); and/or other outside factors that one of ordinary skill in the art would understand a wearable device such as, for instance, wearable device 100 can take in (e.g., capture, collect, receive, measure).

Attachment component 104 according to example embodiments described herein can be used to attach (e.g., affix, fasten) wearable device 100 to a user of wearable device 100. In some embodiments, attachment component 104 can take the form of, for example, a strap, an elastic band, a rope, and/or any other form of attachment one of ordinary skill in the art would understand can be used to attach a wearable device such as, for instance, wearable device 100 to a user.

Securement component 106 according to example embodiments of the present disclosure can facilitate attachment of attachment component 104 upon a user of wearable device 100. In some embodiments, securement component 106 can include, but is not limited to, a pin and hole locking mechanism (e.g., a buckle), a magnet system, a lock, a clip, and/or any other type of securement that one of ordinary skill would understand can be used to facilitate attachment of a wearable device such as, for instance, wearable device 100 to a user. In one embodiment, wearable device 100 does not include securement component 106. For example, in this or another embodiment, wearable device 100 can be secured to a user with a strap that can be tied around the user's wrist and/or another suitable appendage.

Button 108 according to example embodiments described herein can allow for a user to interact with wearable device 100 and/or allow for the user to provide a form of input into wearable device 100. In the example embodiment depicted in FIGS. 1, 2, and 3, one button 108 is shown on wearable device 100. However, it should be appreciated that wearable device 100 is not so limiting. For example, in some embodiments, wearable device 100 can include any number of buttons that allow a user to further interact with wearable device 100 and/or to provide alternative inputs. In at least one embodiment, wearable device 100 does not include button 108. For instance, as described above, in example embodiments, wearable device 100 can include a screen such as, for example, a touch screen that can receive inputs through (e.g., by way of) the touch of the user. In additional or alternative embodiments, wearable device 100 can include a microphone that can receive inputs through (e.g., by way of) voice commands of a user.

In some embodiments, wearable device 100 can constitute a portable computing device that can be designed so that it can be inserted into a wearable case (e.g., as illustrated in the example embodiments depicted in FIGS. 1, 2, and 3). In some embodiments, wearable device 100 can constitute a portable computing device that can be designed so that it can be inserted into one or more of multiple different wearable cases (e.g., a wristband case, a belt-clip case, a pendant case, a case configured to be attached to a piece of exercise equipment such as a bicycle). Wearable device 100 according to embodiments described herein can be formed into one or more shapes and/or sizes to allow for coupling to (e.g., secured to, worn, borne by) the body or clothing of a user. In some embodiments, wearable device 100 can constitute a portable computing device that can be designed to be worn in limited manners such as, for instance, a computing device that is integrated into a wristband in a non-removable manner and/or can be intended to be worn specifically on a person's wrist (or perhaps ankle).

Irrespective of configuration, wearable device 100 according to example embodiments of the present disclosure can include one or more physiological and/or environmental sensors (e.g., internal physiological sensor(s) 143, external physiological sensor(s) 145, and/or MEMS resonator 155) that can be configured to collect physiological and/or environmental data in accordance with various embodiments disclosed herein. In some embodiments, wearable device 100 can be configured to analyze and/or interpret collected physiological and/or environmental data to perform one or more health, wellness, and/or well-being assessments (e.g., physical, mental, emotional, behavioral, and/or sleep quality assessment(s)) of a user (e.g., a wearer) of wearable device 100 according to one or more embodiments described herein. In additional and/or alternative embodiments, wearable device 100 can be configured to communicate with another computing device or server that can perform such one or more health, wellness, and/or well-being assessments (e.g., physical, mental, emotional, behavioral, and/or sleep quality assessment(s)) of a user (e.g., a wearer) of wearable device 100 according to one or more embodiments described herein.

Wearable device 100 in accordance with one or more example embodiments of the present disclosure can include one or more physiological and/or environmental components and/or modules that can be designed to determine one or more physiological and/or environmental metrics associated with a user (e.g., a wearer) of wearable device 100. In at least one embodiment, such physiological and/or environmental component(s) and/or module(s) can constitute and/or include one or more physiological and/or environmental sensors. For instance, although not depicted in the example embodiments illustrated in FIGS. 1, 2, and 3, in some embodiments, wearable device 100 can include one or more physiological and/or environmental sensors such as, for example, an accelerometer, a heart rate sensor (e.g., photoplethysmography (PPG) sensor), an electrodermal activity (EDA) sensor, a body temperature sensor, an environment temperature sensor, and/or another physiological and/or environmental sensor. In these or other embodiments, such physiological and/or environmental sensor(s) can be disposed on, coupled to, and/or otherwise be associated with an underside and/or a backside (e.g., back 134) of wearable device 100.

In some embodiments, the above-described physiological and/or environmental sensor(s) can be disposed on, coupled to, and/or otherwise be associated with wearable device 100 such that the sensor(s) can be in contact with or substantially in contact with human skin when wearable device 100 is worn by a user. For example, in embodiments where wearable device 100 can be worn on a user's wrist, the physiological and/or environmental sensor(s) can be disposed on, coupled to, and/or otherwise be associated with back 134 that can be substantially opposite display 102 and touching an arm of the user. In one embodiment, the above-described physiological and/or environmental sensor(s) can be disposed on, coupled to, and/or otherwise be associated with an interior or skin-side of wearable device 100 (e.g., a side of wearable device 100 that contacts, touches, and/or faces the skin of the user such as, for instance, back 134 and/or bottom 142). In another embodiment, the physiological and/or environmental sensors can be disposed on one or more sides of wearable device 100, including the skin-side (e.g., back 134, bottom 142) and one or more sides (e.g., first side 136, second side 138, top 140, display 102) of wearable device 100 that face and/or are exposed to the ambient environment (e.g., the external environment surrounding wearable device 100).

Importantly, although examples herein are illustrated in the context of a smart watch wearable device, implementations of the present disclosure can be any type or manner of computing device that includes, or is communicatively coupled to, a component contacting a surface that is sufficient to measure thermal noise. For example, the computing devices described herein can be, or otherwise include, wireless earbuds that contact the skin of a user's ears. For another example, the computing devices described herein can be a smart thermostat that contacts a wall of a room. For yet another example, the computing device can be a device included in, or communicatively coupled to, a computing system (e.g., a computing system of a vehicle, etc.) that contacts a surface within the environment in which the computing system is located (e.g., the surface of a seat of a vehicle, a windshield of a vehicle, etc.). As such it should be broadly understood that implementations of the present disclosure can be utilized across a wide variety of use-cases in which the accurate and efficient sensing of the temperature of a surface is desired.

Figure 4:
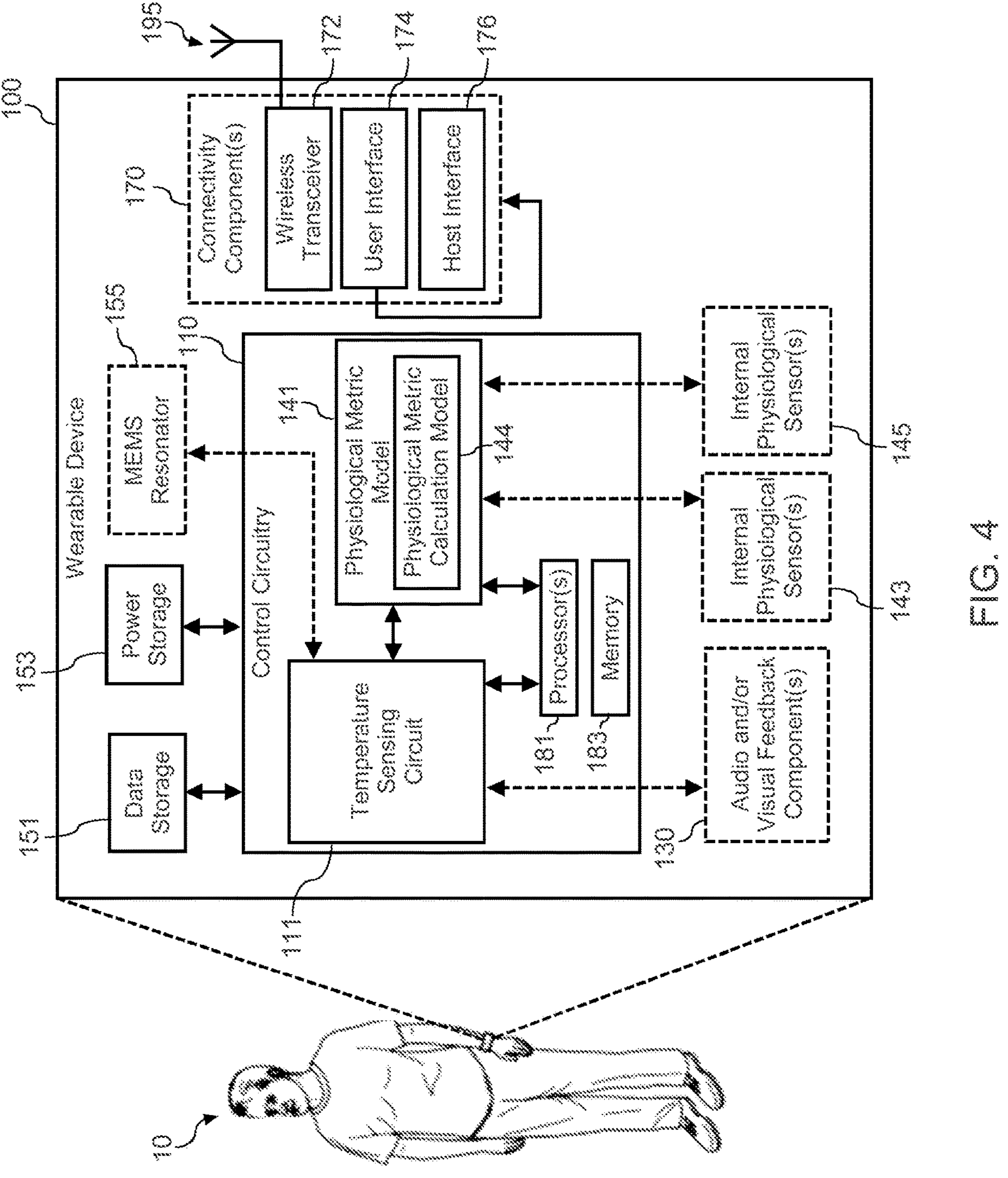
FIG. 4 illustrates a block diagram of the above-described example, non-limiting wearable device according to one or more example embodiments of the present disclosure.

FIG. 4 illustrates a block diagram of the above-described example, non-limiting wearable device 100 according to one or more example embodiments of the present disclosure. That is, for instance, FIG. 4 illustrates a block diagram of one or more internal and/or external components of the above-described example, non-limiting wearable device 100 according to one or more example embodiments of the present disclosure.

As described above with reference to the example embodiments depicted in FIGS. 1, 2, and 3, wearable device 100 can constitute and/or include a wearable device such as, for instance, a wearable physiological monitoring device. For example, in the example embodiment depicted in FIG. 4, wearable device 100 can constitute and/or include a wearable physiological monitoring device that can be worn by a user 10 (also referred to herein as a "wearer" or "wearer 10") and/or can be configured to gather data regarding activities performed by user 10 and/or data regarding user's 10 physiological state (e.g., temperature). In this or another embodiment, such data can include data representative of the ambient environment around user 10 or user's 10 interaction with the environment. For example, in some embodiments, the data can constitute and/or include motion data regarding user's 10 movements, ambient light, ambient noise, air quality, and/or physiological data obtained by measuring various physiological characteristics of user 10 (e.g., heart rate, respiratory data, body temperature, blood oxygen levels, perspiration levels, movement data).

Although certain embodiments are disclosed herein in the context of wearable physiological monitoring devices, it should be appreciated that the present disclosure is not so limiting. For example, it should be understood that one or more embodiments can by performed and/or implemented using any suitable or desirable type of computing device or combination of computing devices such as, for example, a client computing device, a laptop, a tablet, a wearable device (e.g., wearable device 100), a smartphone, and/or another computing device, whether wearable or not.

As illustrated in FIG. 4, wearable device 100 according to example embodiments of the present disclosure can include one or more audio and/or visual feedback components 130 such as, for instance, electronic touchscreen display units, light-emitting diode (LED) display units, audio speakers, light-emitting diode (LED) lights, buzzers, and/or another type of audio and/or visual feedback module. In certain embodiments, one or more audio and/or visual feedback components 130 can be located on and/or otherwise associated with a front side of wearable device 100 and/or display 102. For example, in wearable embodiments of wearable device 100, an electronic display such as, for instance, display 102 can be configured to be externally presented to user 10 viewing wearable device 100.

Wearable device 100 according to example embodiments of the present disclosure can include control circuitry 110. Although certain modules and/or components are illustrated as part of control circuitry 110 in the diagram of FIG. 4, it should be understood that control circuitry 110 associated with wearable device 100 and/or other components or devices in accordance with example embodiments of the present disclosure can include additional components and/or circuitry such as, for instance, one or more additional components of the illustrated components depicted in FIG. 4. Furthermore, in certain embodiments, one or more of the illustrated components of control circuitry 110 can be omitted and/or different than that shown in FIG. 4 and described in association therewith.

The term "control circuitry" is used herein according to its broad and/ordinary meaning and can include any combination of software and/or hardware elements, devices, and/or features that can be implemented in connection with operation of wearable device 100. Furthermore, the term "control circuitry" can be used substantially interchangeably in certain contexts herein with one or more of the terms "controller," "integrated circuit," "IC," "application-specific integrated circuit," "ASIC," "controller chip," or the like.

Control circuitry 110 according to example embodiments of the present disclosure can constitute and/or include one or more processors, data storage devices, and/or electrical connections. In one embodiment, control circuitry 110 can be implemented on a system on a chip (SoC), however, those skilled in the art will recognize that other hardware and/or firmware implementations are possible.

In one or more embodiments of the present disclosure, control circuitry 110 can constitute and/or include one or more processors 181 that can be configured to execute computer-readable instructions that, when executed, cause wearable device 100 to perform one or more operations. In at least one embodiment, control circuitry 110 can constitute and/or include processor(s) 181 that can be configured to execute operational code (e.g., instructions, processing threads, software) for wearable device 100 such as, for instance, firmware or the like. Processor(s) 181 according to example embodiments described herein can each be a processing device. For instance, in the example embodiment depicted in FIG. 4, processor(s) 181 can each be a central processing unit (CPU), microprocessor, microcontroller, integrated circuit (e.g., an application-specific integrated circuit (ASIC)), and/or another type of processing device. In this or another example embodiment, processor(s) 181 can be coupled to (e.g., electrically, communicatively, physically, operatively) to one or more components of control circuitry 110 and/or wearable device 100 such that processor(s) 181 can facilitate one or more operations in accordance with one or more example embodiments described herein.

In at least one embodiment of the present disclosure, the above-described computer-readable instructions and/or operational code that can be executed by processor(s) 181 can be stored in one or more data storage devices of wearable device 100. In the example embodiment depicted in FIG. 4, such computer-readable instructions and/or operational code can be stored in memory 183 of wearable device 100. In this or another example embodiment, memory 183 can be coupled to (e.g., electrically, communicatively, physically, operatively) to one or more components of control circuitry 110 and/or wearable device 100 such that memory 183 can facilitate one or more operations in accordance with one or more example embodiments described herein.

Memory 183 according to example embodiments described herein can store computer-readable and/or computer executable entities (e.g., data, information, applications, models, algorithms) that can be created, modified, accessed, read, retrieved, and/or executed by each of processor(s) 181. In some embodiments, memory 183 can constitute, include, be coupled to (e.g., operatively), and/or otherwise be associated with a computing system and/or media such as, for example, one or more computer-readable media, volatile memory, non-volatile memory, random-access memory (RAM), read only memory (ROM), hard drives, flash drives, and/or other memory devices. In these or other embodiments, such one or more computer-readable media can include, constitute, be coupled to (e.g., operatively), and/or otherwise be associated with one or more non-transitory computer-readable media. Although not depicted in the example embodiment illustrated in FIG. 4, in some embodiments, memory 183 can include (e.g., store) an temperature sensing circuit 111, and/or other modules and/or data that can be used to facilitate one or more operations described herein.

Control circuitry 110 according to example embodiments of the present disclosure can constitute and/or include temperature sensing circuit 111. Temperature sensing circuit 111 according to example embodiments of the present disclosure can constitute and/or include one or more hardware and/or software components and/or features that can be configured to perform temperature sensing for a surface (e.g., the skin of user 10) in accordance with one or more embodiments described herein. For example, in some embodiments, temperature sensing circuit 111 can constitute and/or include one or more hardware and/or software components and/or features that can be configured to sense the temperature of a surface by measuring the degree of thermal noise caused by the surface to a resistor, or other device.

In particular, temperature sensing circuit 111 can include, or can be communicatively coupled to, the MEMS resonator 155 that is configured to generate an output signal indicative of a temperature of a portion of the wearable device 100 that contacts a user's skin when the wearable device 100 is worn by the user. For instance, in some implementations, the portion of the wearable device 100 can be the back 134 of the wearable device 100. In some implementations, the MEMS resonator 155 can be coupled (e.g., via an epoxy material) to an interior surface of the back 134 of the wearable device 100. In this manner, the MEMS resonator 155 can be disposed within a cavity (not shown) defined by the wearable device 100 and therefore be hidden from the user's view. In alternative implementations, the MEMS resonator 155 can be integrally formed with the back 134 of the wearable device 100.

It should be appreciated, however, that the MEMS resonator can be located on any suitable portion of the wearable device 100 that contacts the user's skin when the wearable device 100 is worn by the user. It should also be appreciated that the portion of the wearable device 100 that contacts the user's skin when the wearable device 100 is worn by the user is formed from a thermoelectric material. For instance, in some implementations, the portion of the wearable device 100 can be formed from a metal material.

In one embodiment, temperature sensing circuit 111 can constitute and/or include one or more of the ML and/or AI models 113 described herein (e.g., a classifier) that can identify such a correlation or absence of correlation between the sensed temperature and potential causes of the sensed temperature at the surface of the user 10. In one embodiment, wearable device 100 can train such ML and/or AI model(s) 113 as described herein using the above-described annotated physiological dataset. In one embodiment, wearable device 100 can implement (e.g., execute, run) such ML and/or AI model(s) 113 to identify such a correlation or absence of correlation between the between the sensed temperature and potential causes of the sensed temperature at the surface of the user 10 (e.g., hypothermia, hyperthermia, fever, exertion, weather, etc.).

In some embodiments, based at least in part on (e.g., in response to) sensing a surface temperature, wearable device 100 can perform one or more operations described herein to facilitate alteration (e.g., improvement) of user's 10 health, wellness, and/or well-being (e.g., physical, mental, emotional, behavioral, and/or sleep quality). For example, in at least one embodiment, wearable device 100 can perform operation(s) that can include, but not limited to: presenting the sensed temperature to user 10 and/or another computing device; providing user 10 and/or another computing device with an explanation of the sensed temperature, which can include a defined activity as described herein, suggesting one or more health improvement recommendations and/or engage another computing device to make such recommendation(s) based at least in part on (e.g., using) the sensed temperature (e.g., recommendation that user 10 seek medical attention, or seek epidemiological testing); implementing one or more wellness promoting features and/or engage another computing device to implement such feature(s) based at least in part on (e.g., using) the correlation or absence of correlation (e.g., vibrating in a particular manner to indicate to a user that they should reduce physical exertion, etc.); and/or another operation according to one or more example embodiments of the present disclosure.

In certain embodiments, physiological metric module 141 and/or physiological metric calculation module 144 can be communicatively coupled with one or more internal physiological sensors 143 that can be embedded and/or integrated in wearable device 100. In certain embodiments, physiological metric module 141 and/or physiological metric calculation module 144 can be optionally in communication with one or more external physiological sensors 145 not embedded and/or integrated in wearable device 100 (e.g., an electrode or sensor integrated in another electronic device). In some embodiments, examples of internal physiological sensors 143 and/or external physiological sensors 145 can constitute and/or include, but are not limited to, one or more sensors that can measure (e.g., capture, collect, receive) physiological data of user 10 such as, for instance, heart rate, blood oxygen level, movement, respiration, perspiration, stress data, and/or other physiological data of user 10. In some implementations, the MEMS resonator 155 and/or the temperature sensing circuit 111 can be an external physiological sensor(s) 145.

In the example embodiment depicted in FIG. 4, wearable device 100 can include one or more data storage components 151 (denoted as "data storage 151" in FIG. 4). Data storage component(s) 151 according to example embodiments can constitute and/or include any suitable or desirable type of data storage such as, for instance, solid-state memory, which can be volatile or non-volatile. In some embodiments, such solid-state memory of wearable device 100 can constitute and/or include any of a wide variety of technologies such as, for instance, flash integrated circuits, phase change (PC) memory, phase change (PC) random-access memory (RAM), programmable metallization cell RAM (PMC-RAM or PMCm), ovonic unified memory (OUM), resistance RAM (RRAM), NAND memory, NOR memory, EEPROM, ferroelectric memory (FeRAM), MRAM, or other discrete NVM (non-volatile solid-state memory) chips. In some embodiments, data storage component(s) 151 can be used to store system data, such as operating system data and/or system configurations or parameters. In some embodiments, wearable device 100 can include data storage utilized as a buffer and/or cache memory for operational use by control circuitry 110.

Data storage component(s) 151 according to example embodiments can include various sub-modules that can be implemented to facilitate the physiological monitoring and the health, wellness, and/or well-being assessment principles and features disclosed herein (e.g., temperature sensing) in accordance with one or more embodiments. For example, in at least one embodiment, data storage 151 can include one or more sub-modules that can include, but not limited to: an information collection module (e.g., physiological metric module 141, physiological metric calculation module 144) that can manage the collection of physiological and/or environmental data relevant to any health, wellness, and/or well-being assessment described herein (e.g., body temperature sensing); a heart rate determination module that can determine values and/or patterns of one or more types of heart rates of user 10; a condition determination module that can determine a condition that may cause the temperature at the surface of the user 10 (e.g., the user's skin), such as a disease, hyperthermia, hypothermia, exercise, etc.); a presentation module that can manage presentation of information to user 10 that can be associated with any health, wellness, and/or well-being assessment described herein (e.g., body temperature); a feedback management module for collecting and interpreting any input data and/or feedback received from user 10 (e.g., information associated with user's 10 body temperature); and/or another sub-module.

Wearable device 100 according to example embodiments can further include a power storage module 153 (denoted as "power storage 153"), which can constitute and/or include a rechargeable battery, one or more capacitors, or other charge-holding device(s). In some embodiments, the power stored by power storage module 153 can be utilized by control circuitry 110 for operation of wearable device 100, such as for powering display 102. In some embodiments, power storage module 153 can receive power over a host interface of wearable device 100 (e.g., via one or more host interface circuitry and/or components 176 (denoted as "host interface 176" in FIG. 4)) and/or through other means.

Wearable device 100 according to example embodiments can further include one or more connectivity components 170, which can include, for example, a wireless transceiver 172. Wireless transceiver 172 according to example embodiments can be communicatively coupled to one or more antenna devices 195, which can be configured to wirelessly transmit and/or receive data and/or power signals to and/or from wearable device 100 using, but not limited to, peer-to-peer, WLAN, and/or cellular communications. For example, wireless transceiver 172 can be utilized to communicate data and/or power between wearable device 100 and an external computing device (not illustrated in FIG. 4) such as, for instance, an external client computing device (e.g., a smartphone, tablet, computer) and/or an external host system (e.g., a server), which can be configured to interface with wearable device 100. In certain embodiments, wearable device 100 can include one or more host interface circuitry and/or components 176 (denoted as "host interface 176" in FIG. 4) such as, for instance, wired interface components that can communicatively couple wearable device 100 with the above-described external computing device (e.g., a smartphone, table, computer, server) to receive data and/or power therefrom and/or transmit data thereto.

Connectivity component(s) 170 according to example embodiments can further include one or more user interface components 174 (denoted as "user interface 174" in FIG. 4) that can be used by wearable device 100 to receive input data from user 10 and/or provide output data to user 10. In some embodiments, user interface component(s) 174 can be coupled to (e.g., operatively, communicatively) and/or otherwise be associated with audio and/or visual feedback component(s) 130. For instance, in these embodiments, display 102 of wearable device 100 can constitute and/or include a touchscreen display that can be configured to provide (e.g., render) output data to user 10 and/or to use audio and/or visual feedback component(s) 130 to receive user input through user contact with the touchscreen display. In some embodiments, user interface component(s) 174 can further constitute and/or include one or more buttons or other input components or features.

Connectivity component(s) 170 according to example embodiments can further include host interface circuitry and/or component(s) 176, which can be, for example, an interface that can be used by wearable device 100 to communicate with the above-described external computing device (e.g., a smartphone, table, computer, server) over a wired or wireless connection. Host interface circuitry and/or component(s) 176 according to example embodiments can utilize and/or otherwise be associated with any suitable or desirable communication protocol and/or physical connector such as, for instance, universal serial bus (USB), micro-USB, Wi-Fi, Bluetooth, Fire Wire, PCIe, or the like. For wireless connections, host interface circuitry and/or component(s) 176 according to example embodiments can be incorporated with wireless transceiver 172.

Although certain functional modules and components are illustrated and described herein, it should be understood that authentication management functionality in accordance with the present disclosure can be implemented using a number of different approaches. For example, in some embodiments, control circuitry 110 can constitute and/or include one or more processors (e.g., processor(s) 181) that can be controlled by computer-executable instructions that can be stored in a memory (e.g., memory 183, data storage component(s) 151) so as to provide functionality such as is described herein. In other embodiments, such functionality can be provided in the form of one or more specially designed electrical circuits. In some embodiments, such functionality can be provided by one or more processors (e.g., processor(s) 181) that can be controlled by computer-executable instructions that can be stored in a memory (e.g., memory 183, data storage component(s) 151) that can be coupled to (e.g., communicatively, operatively, electrically) one or more specially designed electrical circuits. Various examples of hardware that can be used to implement the concepts outlined herein can include, but are not limited to, application specific integrated circuits (ASICs), field-programmable gate arrays (FPGAs), and general-purpose microprocessors that can be coupled with memory that stores executable instructions for controlling the general-purpose microprocessors.

Figure 5:
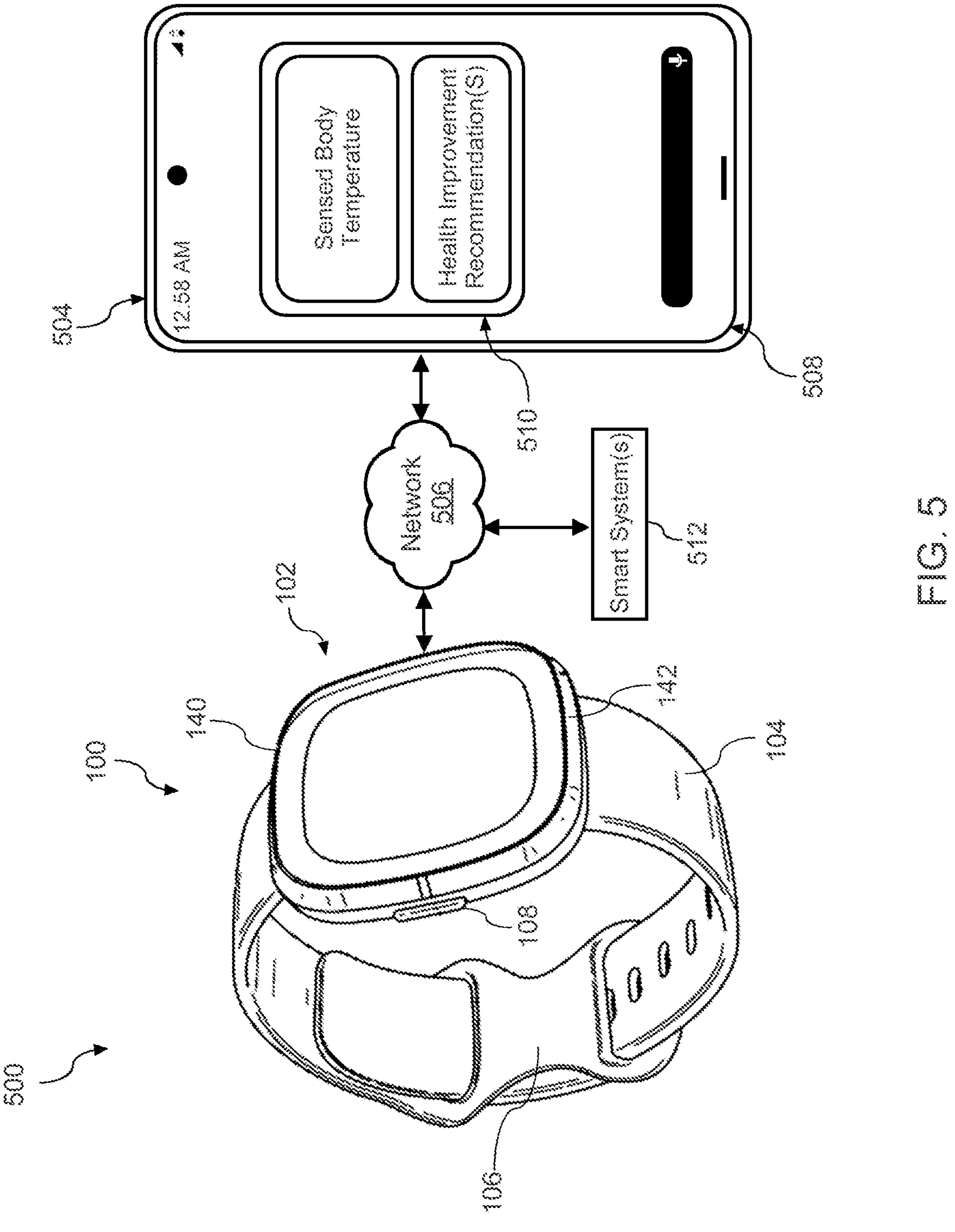
FIG. 5 illustrates a diagram of an example, non-limiting user assessment management system according to one or more example embodiments of the present disclosure.

FIG. 5 illustrates a diagram of an example, non-limiting user assessment management system 500 according to one or more example embodiments of the present disclosure. User assessment management system 500 depicted in FIG. 5 illustrates an example, non-limiting networked relationship between wearable device 100, an external computing device 504, and/or one or more smart systems 512 in accordance with one or more embodiments.

With reference to the example embodiment described above and depicted in FIG. 4, wearable device 100 according to example embodiments of the present disclosure can perform one or more health, wellness, and/or well-being assessments (e.g., physical, mental, emotional, behavioral, and/or sleep quality assessment(s)) of user 10 and/or perform operation(s) to facilitate alteration (e.g., improvement) of user's 10 health, wellness, and/or well-being based on such assessment(s). As such, in certain embodiments described in the present disclosure, wearable device 100 can be capable of and/or configured to collect physiological sensor readings of user 10 and/or perform such assessment(s) and/or operation(s) using such readings.

However, in additional and/or alternative embodiments, wearable device 100 and/or another electronic and/or computing device that can be used to detect physiological information of user 10, can be in communication with external computing device 504. In these and/or other embodiments, external computing device 504 can be configured to use such physiological information of user 10 to perform such one or more health, wellness, and/or well-being assessments (e.g., body temperature sensing) of user 10 according to one or more embodiments described herein. In these and/or other embodiments, based at least in part on (e.g., in response to) performing such assessment(s), external computing device 504 can perform one or more operations described herein to facilitate alteration (e.g., improvement) of user's 10 health, wellness, and/or well-being (e.g., physical, mental, emotional, behavioral, and/or sleep quality).

Wearable device 100 according to example embodiments can be configured to collect one or more types of physiological and/or environmental data using embedded sensors and/or external devices, as described throughout the present disclosure, and communicate or relay such information over one or more networks 506 to other devices. This includes, in some embodiments, relaying information to devices capable of serving as Internet-accessible data sources, thus permitting the collected data to be viewed, for example, using a web browser or network-based application at, for instance, external computing device 504. For example, while user 10 is wearing wearable device 100, wearable device 100 can capture, calculate, and/or store environment data and/or user's 10 physiological data (e.g., heart rate, motion data, temperature, respiration, perspiration, EDA, stress data) using one or more environmental and/or physiological sensors. Wearable device 100 according to example embodiments can then transmit data representative of such environment data and/or user's 10 physiological data over network(s) 506 to an account on a web service, computer, mobile phone, and/or health station where the data can be stored, processed, and visualized by user 10 and/or another entity (e.g., a health care professional).

While wearable device 100 is shown in example embodiments of the present disclosure to have a display, it should be understood that, in some embodiments, wearable device 100 does not have any type of display unit. In some embodiments, wearable device 100 can have audio and/or visual feedback components such as, for instance, light-emitting diodes (LEDs), buzzers, speakers, and/or a display with limited functionality. Wearable device 100 according to example embodiments can be configured to be attached to user's 10 body or clothing. For example, in these or other embodiments, wearable device 100 can be configured as a wrist bracelet, watch, ring, electrode, finger-clip, toe-clip, chest-strap, ankle strap, and/or a device placed in a pocket. In additional or alternative embodiments, wearable device 100 can be embedded in something in contact with user 10 such as, for instance, clothing, a mat that can be positioned under user 10, a blanket, a pillow, and/or another accessory.

In one or more embodiments of the present disclosure, the communication between wearable device 100 and external computing device 504 can be facilitated by network(s) 506. In some embodiments, network(s) 506 can constitute and/or include, for instance, one or more of an ad hoc network, a peer-to-peer communication link, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the public switched telephone network (PSTN), a cellular telephone network, and/or any other type of network. In some embodiments, the communication between wearable device 100 and external computing device 504 can also be performed through a direct wired connection. In these or other embodiments, this direct-wired connection can be associated with any suitable or desirable communication protocol and/or physical connector such as, for instance, universal serial bus (USB), micro-USB, Wi-Fi, Bluetooth, Fire Wire, PCIe, or the like.

In example embodiments of the present disclosure, a variety of computing devices can be in communication with wearable device 100 to facilitate user's 10 health, wellness, and/or well-being assessment and/or alteration (e.g., improvement). Although external computing device 504 is depicted as a smartphone in the example embodiment illustrated in FIG. 5, it should be understood that the present disclosure is not so limiting. For instance, external computing device 504 according to example embodiments can constitute and/or include, for example, a smartphone with a display 508 as depicted in FIG. 5, a personal digital assistant (PDA), a mobile phone, a tablet, a personal computer, a laptop computer, a smart television, a video game console, a server, and/or another computing device that can be external to wearable device 100.

The networked relationship depicted in the example embodiment illustrated in FIG. 5 demonstrates how, in some embodiments, external computing device 504 can be implemented to perform one or more health, wellness, and/or well-being assessments (e.g., a body temperature assessment) of user 10 and/or perform operation(s) to facilitate alteration (e.g., improvement) of user's 10 health, wellness, and/or well-being based on such assessment(s). For example, in one embodiment, user 10 can wear wearable device 100 that can be equipped as a bracelet with one or more physiological sensors but without a display. In this and/or another embodiment, while user 10 is wearing wearable device 100, wearable device 100 can capture, calculate, and/or store environment data and/or user's 10 physiological data (e.g., temperature) using the physiological sensors.

Wearable device 100 according to example embodiments can then transmit data representative of such environment data and/or user's 10 physiological data over network(s) 506 to an account on a web service, computer, mobile phone, and/or health station where the data can be stored, processed, and visualized by user 10 and/or another entity (e.g., a health care professional). In some embodiments, wearable device 100 can periodically or continuously transmit such information to external computing device 504 over network(s) 506.

In additional and/or alternative embodiments, wearable device 100 can store the above-described collected physiological and/or environmental data and transmit this data to external computing device 504 in response to a trigger event such as, for instance, detection of an abnormal surface temperature of the skin of the user 10 (e.g., above or below a threshold range of standard human temperatures) after a period performing the defined activity. In some embodiments, wearable device 100 can transmit such data to external computing device 504 in response to detecting that a command has been performed by external computing device 504 such as, for instance, manual or automatic execution of an instruction to synchronize collected physiological and/or environmental data and perform one or more health, wellness, and/or well-being assessments (e.g., body temperature assessment) of user 10 as described herein.

In some embodiments, external computing device 504 can present (e.g., provide, render) a possible cause of the body temperature of user 10. For instance, in these or other embodiments, external computing device 504 can generate an intelligent notification 510 that can include such body temperature and/or one or more health improvement recommendations (e.g., a suggestion to reduce physical activity, a suggestion to see a healthcare provider, etc.) that, if and/or when implemented by user 10, can facilitate alteration (e.g., improvement) of user's 10 health, wellness, and/or well-being (e.g., body temperature). In the example embodiment depicted in FIG. 5, external computing device 504 can render intelligent notification 510 having such body temperature and the health improvement recommendation(s) on display 508 such that user 10 and/or another entity (e.g., health care professional, mental health care professional, sleep therapy provider, doctor, caregiver) can view such information.

Although not illustrated in the example embodiment depicted in FIG. 5, in some embodiments, wearable device 100 can: sense a body temperature of the user 10; determine one or more health improvement recommendations based on (e.g., in response to) sensing the body temperature; generate intelligent notification 510 such that it includes the body temperature and the health improvement recommendation(s); and render this information on display 102 of wearable device 100.

In one embodiment of the present disclosure, wearable device 100 and/or external computing device 504 can implement (e.g., initiate, run, operate) one or more wellness promoting features that can be included with wearable device 100 and/or external computing device 504 such as, for instance, a wellness promoting audio feature (e.g., by playing a sound that alerts the user to the occurrence of an abnormal body temperature), and/or another wellness promoting feature of wearable device 100 and/or external computing device 504.

In another embodiment of the present disclosure, wearable device 100 and/or external computing device 504 can facilitate implementation of one or more wellness promoting features of another computing device such as, for instance, a computing device of one or more smart systems 512. In this or another embodiment, smart system(s) 512 can constitute and/or include, but are not limited to, an audio system (e.g., a home audio system), a lighting system (e.g., a home lighting system), an HVAC system (e.g., a home HVAC system), an exercise system (e.g., an exercise machine), and/or another system that can be included in, coupled to, and/or operated by a computing device other than wearable device 100 and/or external computing device 504. For instance, in some embodiments, smart system(s) 512 can constitute and/or include a smart audio system, a smart lighting system, a smart HVAC system, and/or a smart exercise system (e.g., a smart exercise machine). In these or other embodiments, wearable device 100 and/or external computing device 504 can facilitate implementation of one or more wellness promoting features of smart system(s) 512 such as, for instance: a wellness promoting audio feature of a smart audio system; a wellness promoting lighting feature of a smart lighting system; a wellness promoting ambient temperature feature of a smart HVAC system; a wellness promoting exercise feature (e.g., a certain exercise mode or setting) of a smart exercise system; and/or another wellness promoting feature of smart system(s) 512.

In some embodiments described herein, wearable device 100 and/or external computing device 504 can send instructions to smart system(s) 512 that, when executed by such system(s) (e.g., via one or more processors), can cause the system(s) to perform operations to implement one or more wellness promoting features of such system(s). In one embodiment, wearable device 100 and/or external computing device 504 can send instructions to a smart audio system that, when executed by such a system (e.g., via one or more processors), can cause it to inform the user 10 that an abnormal body temperature has been detected. In another embodiment, wearable device 100 and/or external computing device 504 can send instructions to a smart HVAC system that, when executed by such a system (e.g., via one or more processors), can cause it to output air at a certain wellness promoting temperature (e.g., a certain temperature that can be defined by user 10). In one embodiment of the present disclosure, wearable device 100 and/or external computing device 504 can send instructions to a smart exercise system that, when executed by such a system (e.g., via one or more processors), can cause it to operate in a certain mode or setting and/or to provide a recommendation to the user to select such a mode or setting.

Figure 6:
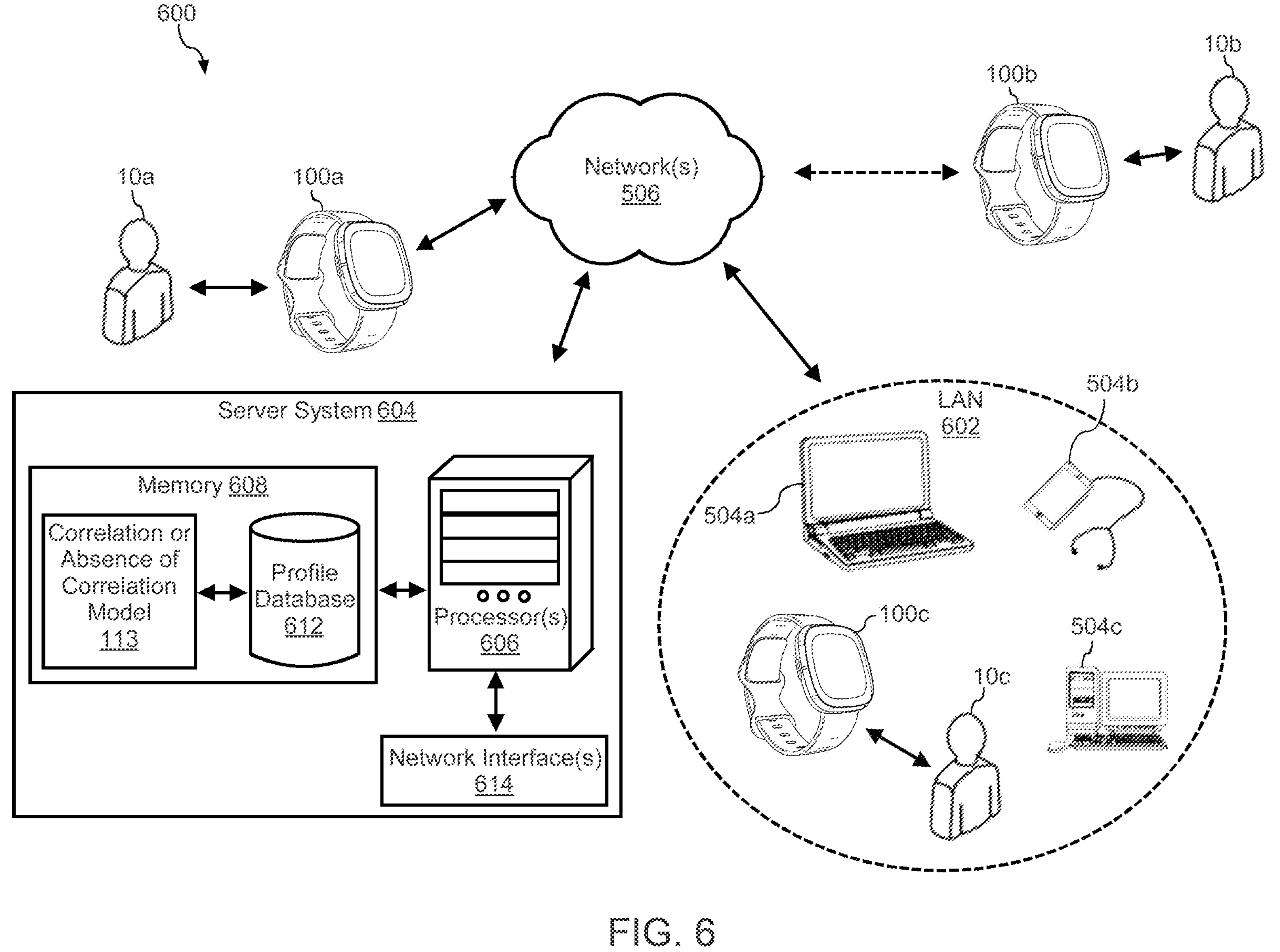
FIG. 6 illustrates a diagram of an example, non-limiting user assessment management system according to one or more example embodiments of the present disclosure.

FIG. 6 illustrates a diagram of an example, non-limiting user assessment management system 600 according to one or more example embodiments of the present disclosure. User assessment management system 600 depicted in FIG. 6 illustrates an example, non-limiting networked relationship between one or more wearable devices 100*a*, 100*b*, 100*c*, one or more external computing devices 504*a*, 504*b*, 504*c*, and/or a server system 604 in accordance with one or more embodiments.

In the example embodiment depicted in FIG. 6, wearable devices 100*a*, 100*b*, 100*c* can each include the same characteristics, structure, components, attributes, and/or functionality as that of wearable device 100. In this embodiment, each wearable device 100*a*, 100*b*, 100*c* can be coupled to (e.g., worn by) a respective user 10*a*, 10*b*, 10*c*. In this embodiment, external computing devices 504*a* (e.g., a laptop computer), 504*b* (e.g., a smartphone), 504*c* (e.g., a personal computer) can each include the same characteristics, structure, components, attributes, and/or functionality as that of external computing device 504.

In some embodiments of the present disclosure, network(s) 506 can couple (e.g., communicatively) one or more of wearable devices 100*a*, 100*b*, 100*c* to server system 604 and/or one or more of external computing devices 504*a*, 504*b*, 504*c*. In some embodiments, one or more of external computing devices 504*a*, 504*b*, 504*c* and/or one or more of wearable devices 100*a*, 100*b*, 100*c* can be interconnected in a local area network (LAN) 602 or another type of communication interconnection that can be connected to (e.g., communicatively coupled to) network(s) 506. LAN 602 according to example embodiments can interconnect one or more of external computing devices 504*a*, 504*b*, 504*c*, as well as one or more of wearable devices 100*a*, 100*b*, 100*c*. In some embodiments, one or more of wearable devices 100*a*, 100*b*, 100*c* and/or one or more of external computing devices 504*a*, 504*b*, 504*c* can be connected to (e.g., communicatively coupled to) network(s) 506 and/or server system 604, indirectly, through LAN 602. In some embodiments, one or more of wearable devices 100*a*, 100*b*, 100*c* can be directly connected to (e.g., communicatively coupled to) network(s) 506 and/or indirectly connected to network(s) 506 through LAN 602. For instance, in the example embodiment depicted in FIG. 6, wearable device 100*b* can be connected to (e.g., communicatively coupled to) external computing device 504*b* (e.g., a smartphone) through, for example, a Bluetooth connection. In this embodiment, external computing device 504*b* can be connected to (e.g., communicatively coupled to) server system 604 through network(s) 506 and wearable device 100*b* can also be connected to (e.g., communicatively coupled to) server system 604 through network 506.

In the example embodiment depicted in FIG. 6, server system 604 can collect detected physiological and/or environmental sensor readings from one or more of wearable devices 100*a*, 100*b*, 100*c*. In some embodiments, server system 604 can also collect from one or more of wearable devices 100*a*, 100*b*, 100*c* and/or from one or more of external computing devices 504*a*, 504*b*, 504*c*, body temperatures of one or more users 10*a*, 10*b*, 10*c*, etc.

For example, in the embodiment depicted in FIG. 6, wearable device 100*a* is not associated with an external computing device, therefore wearable device 100*a* can transmit physiological data of user 10*a* (e.g., a body temperature) to server system 604. In this embodiment, server system 604 can analyze the received data to identify a correlation or absence of correlation between a body temperature of user 10*a* and at least one activity performed by user 10*a* at a certain. In this embodiment, server system 604 can transmit an intelligent notification (e.g., intelligent notification 510), the body temperature of user 10*a*, and/or one or more health improvement recommendations back to wearable device 100*a*.

As another example, in the embodiment depicted in FIG. 6, wearable device 100*b* can transmit physiological data of user 10*b* to server system 604 and external computing device 504*a*. In this embodiment, external computing device 504*a* can analyze the received data to identify a body temperature of user 10*b* and at least one health condition associated with user 10*b*. In this embodiment, server system 604 can use the received physiological data (e.g., body temperature) of user 10*b* to update a user profile for user 10*b* that can be stored in a profiles database 612 (e.g., a log) that can be stored on a memory 608 that can be included in, coupled to, and/or otherwise associated with server system 604.

In some embodiments, server system 604 can be implemented on one or more standalone data processing apparatuses or a distributed network of computers. In some embodiments, server system 604 can employ various virtual devices and/or services of third-party service providers (e.g., third-party cloud service providers) to provide the underlying computing resources and/or infrastructure resources of server system 604. In some embodiments, server system 604 can include, but is not limited to, a handheld computer, a tablet computer, a laptop computer, a desktop computer, or a combination of any two or more of these data processing devices or other data processing devices.

Server system 604 according to example embodiments can include one or more processors 606 (e.g., processing unit(s), denoted as "processor(s) 606" in FIG. 6) such as, for instance, one or more CPUs. In these or other embodiments, server system 604 can include one or more network interfaces 614 that can include, for example, an input/output (I/O) interface to external computing device 504*a*, 504*b*, and/or 504*c* and/or wearable devices 100*a*, 100*b*, and/or 100*c*. In some embodiments, server system 604 can include memory 608, and one or more communication buses for interconnecting these components.

Memory 608 according to example embodiments can include high-speed random-access memory such as, for instance, DRAM, SRAM, DDR RAM, or other random-access solid-state memory devices; and, optionally, can include non-volatile memory such as, for example, one or more magnetic disk storage devices, one or more optical disk storage devices, one or more flash memory devices, or one or more other non-volatile solid state storage devices. Memory 608 according to example embodiments, optionally, can include one or more storage devices that can be remotely located from processor(s) 606 (e.g., processing unit(s)). Memory 608 according to example embodiments, or alternatively the non-volatile memory within memory 608, can include a non-transitory computer readable storage medium. In some embodiments, memory 608, or the non-transitory computer readable storage medium of memory 608, can store one or more programs, modules, and data structures. In these embodiments, such programs, modules, and data structures can include, but not be limited to, one or more of an operating system that can include procedures for handling various basic system services and for performing hardware dependent tasks, a network communication module for connecting server system 604 to other computing devices (e.g., wearable device 100*a*, 100*b*, and/or 100*c* and/or external computing device 504*a*, 504*b*, and/504*c*) connected to network(s) 506 via network interface(s) 614 (e.g., wired or wireless).

Memory 608 according to example embodiments can also include profiles database 612 that can store user profiles for users 10*a*. 10*b*, 10*c*. In some embodiments, a respective user profile for a user can include, for instance: a user identifier (e.g., an account name or handle); login credentials (e.g., login credentials to user assessment management system 600); email address or preferred contact information; wearable device information (e.g., model number); demographic parameters for the user (e.g., age, gender, occupation); historical physiological data of the user; historical correlations or absences of correlation between trigger events and moods experienced by the user; and/or identified health, wellness, and/or well-being metrics and/or trends of the user (e.g., body temperature of the user).

In some embodiments, a user can opt in or opt out of providing health, wellness, and/or well-being assessment information (e.g., physical, mental, emotional, behavioral, and/or sleep quality assessment information) to a population-normalization determination for other users. In some embodiments, a user's health, wellness, and/or well-being assessment information (e.g., body temperature) can be incorporated into population-normalized health, wellness, and/or well-being metric and/or trend information (e.g., physical, mental, emotional, behavioral, and/or sleep quality metric and/or trend information) used to determine that user's own values for one or more health, wellness, and/or well-being metrics and/or trends (e.g., physical, mental, emotional, behavioral, and/or sleep quality metrics and/or trends).

In at least one embodiment described herein, server system 604 can record, in profiles database 612, the health, wellness, and/or well-being assessment information (e.g., body temperature information) respectively corresponding to users 10*a*, 10*b*, 10*c*. In example embodiments of the present disclosure, with respect to each of such users 10*a*, 10*b*, 10*c*, such health, wellness, and/or well-being assessment information can include a plurality of body temperatures. In some embodiments, with respect to each of such users 10*a*, 10*b*, 10*c*, such health, wellness, and/or well-being assessment information can include the above-described annotated physiological dataset that can be used to train an ML and/or AI model described herein to identify such a plurality of correlations and plurality of absences of correlation.

Figure 7:
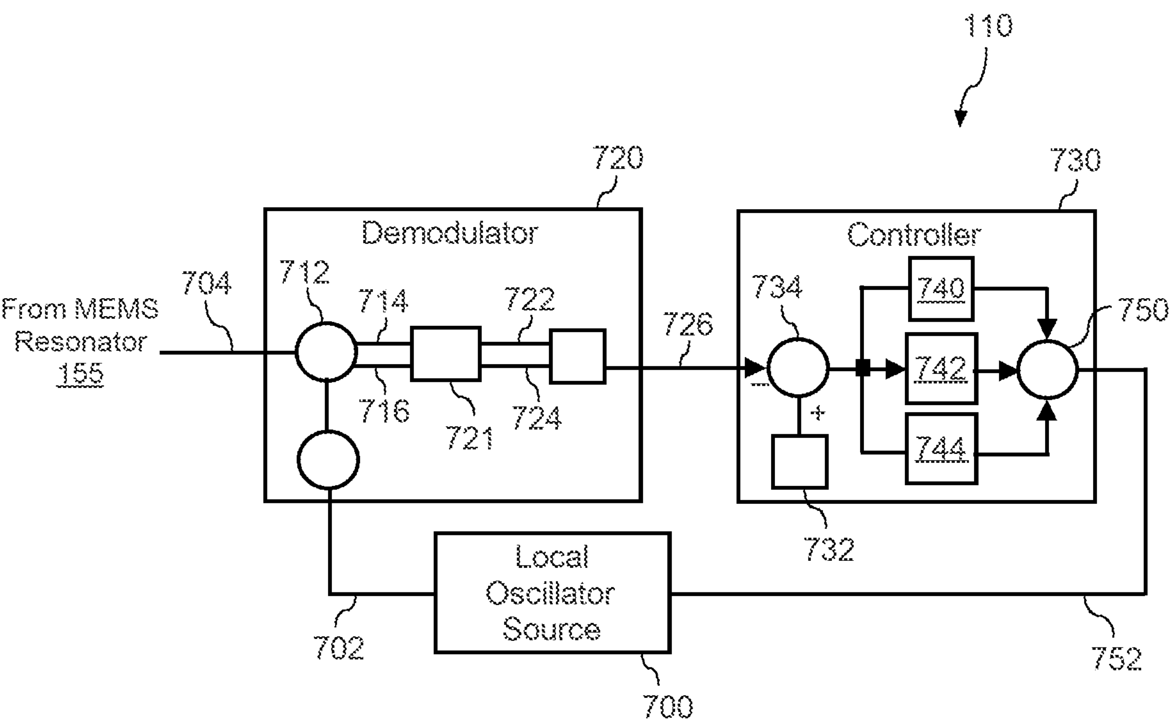
FIG. 7 depicts a block diagram of components of control circuitry of a wearable computing device according to some implementations of the present disclosure.

Referring now to FIG. 7, a block diagram of components of the control circuitry 110 is provided according to some implementations of the present disclosure. As shown, the control circuitry 110 can include a local oscillator source 700 (e.g., numerically controlled oscillator) configured to generate an initial local oscillator signal 702. For instance, in some implementations, the initial local oscillator signal 702 can correspond to an initial setpoint temperature for the portion of the wearable device 100 (FIG. 2) that contacts the user's skin when the wearable device 100 is worn by the user. In some implementations, the initial setpoint temperature can be defined during manufacturing of the wearable device 100 and can therefore be replicated across all wearable devices having the MEMS resonator 155 for temperature sensing.

The control circuitry 110 can include a demodulator 710. As shown, the demodulator 710 can be configured to receive the initial local oscillator signal 702 from the local oscillator source 700 and an output signal 704 from the MEMS resonator 155 (FIG. 2). In some implementations, the demodulator 710 can include a mixer 712. As shown, the mixer 712 can receive the initial local oscillator signal 702 as a first input and the output signal 704 as a second input. Furthermore, the mixer 712 can be configured to output a first signal 714 and a second signal 716. The demodulator 710 can further include a filter 721 configured to filter the first signal 714 and the second signal 716. As shown, the filter 721 can filter the first signal 714 and output a first filtered signal 722 (e.g., demodulated output signal). Likewise, the filter 721 can filter the second signal 716 and output a second filtered signal 724 (e.g., demodulated local oscillator signa).

In some implementations, the demodulator 710 can be configured to output a phase difference 726 between a phase of the first filtered signal 722 and a phase of the second filtered signal 724. It should be appreciated that the phase difference between the output signal 704 (e.g., first filtered signal 722) and the initial local oscillator signal 702 (e.g., second filtered signal 724) can be due, at least in part, to a change in the temperature of the portion (e.g., back 134) of the wearable device 100.

The control circuitry 110 can include a controller 730. The controller 730 can be configured to generate a setpoint 732 associated with a phase of the initial local oscillator signal 702. Furthermore, the controller 730 can be configured to receive the phase difference 726 and determine whether a differential 734 between the phase difference 726 and the setpoint 732 is non-zero. For instance, the controller 730 can include a difference block 735 that receives the phase difference 726 and the setpoint 732 as separate inputs and outputs the differential 734.

When the controller 730 determines the differential 734 between the phase difference 726 and the setpoint 732 is non-zero, the controller 730 can determine the temperature of the portion of the wearable device 100 has changed (e.g., increased or decreased). Furthermore, the change in temperature of the portion of the wearable device 100 can indicate a change to the temperature of the user's skin since the user's skin contacts the portion of the wearable device 100. In this manner, the control circuitry 110 can determine the change to the temperature of the user's skin based, at least in part, on the phase difference 726 between the initial local oscillator signal 702 generated by the local oscillator source 700 and the output signal 704 generated by the MEMS resonator 155.

In some implementations, the controller 730 can be configured to generate one or more commands associating with adjust the initial local oscillator signal 702 as needed to eliminate the phase difference 726. In this manner, the control circuitry 110 can be configured to sense another temperature change (e.g., increase or decrease) for the portion of the wearable device 100 and therefore determine a change to the temperature of the user's skin.

In some implementations, the controller 730 can be a proportional integral derivative (PID) controller. In such implementations, the differential 734 can be provided to each of a proportional block 740, an integral block 742, and a derivative block 744 of the PID controller. Furthermore, the output from each of the proportional block 740, integral block 742, and derivative block 744 can be provided to a summation block 750 and an output 752 (e.g., summation of the output from blocks 740, 742, 744) of the summation block 750 can be provided to the local oscillator source 700. It should be appreciated that the output 752 of the summation block 750 can be associated with adjusting the initial local oscillator signal 702 output by the local oscillator source 700 as needed to eliminate the phase difference 726. In this manner, the control circuitry 110 can return to a steady-state and can be ready to sense another change (e.g., increase or decrease) in the temperature of the skin of the user wearing the wearable device 100.

In some implementations, the control circuitry 110 can be configured to determine whether a change to the skin temperature of the user is above a threshold temperature (e.g., 98.6° F.) by a predetermined amount of below the threshold temperature by a predetermined amount. Furthermore, in such implementations, the control circuitry 110 can be configured to generate a notification (e.g., audio or visual) indicative of the user's skin temperature being above or below the predetermined amount. For instance, in some implementations, the notification can be indicative of the user running a fever (e.g., temperature over 100° F.).

In some implementations, the output signal 704 from the MEMS resonator 155 can be provided to the processor(s) 181 (FIG. 4) of the wearable device 100 and can be used to clock the processor(s) 181. In this manner, the MEMS resonator 155 can function as both a temperature sensor and a clock source for the wearable device 100.

It should be appreciated that the local oscillator source 700, demodulator 720, and controller 730 can collectively be implemented as a phase-locked loop circuit. It should also be appreciated that the temperature sensing circuit 111 (FIG. 4) of the control circuitry 110 can include one or more components discussed herein with reference to FIG. 7. For instance, the temperature sensing circuit 111 can include at least one of the local oscillator source 700, the demodulator 720, or the controller 730.

Example Method

Figure 8:
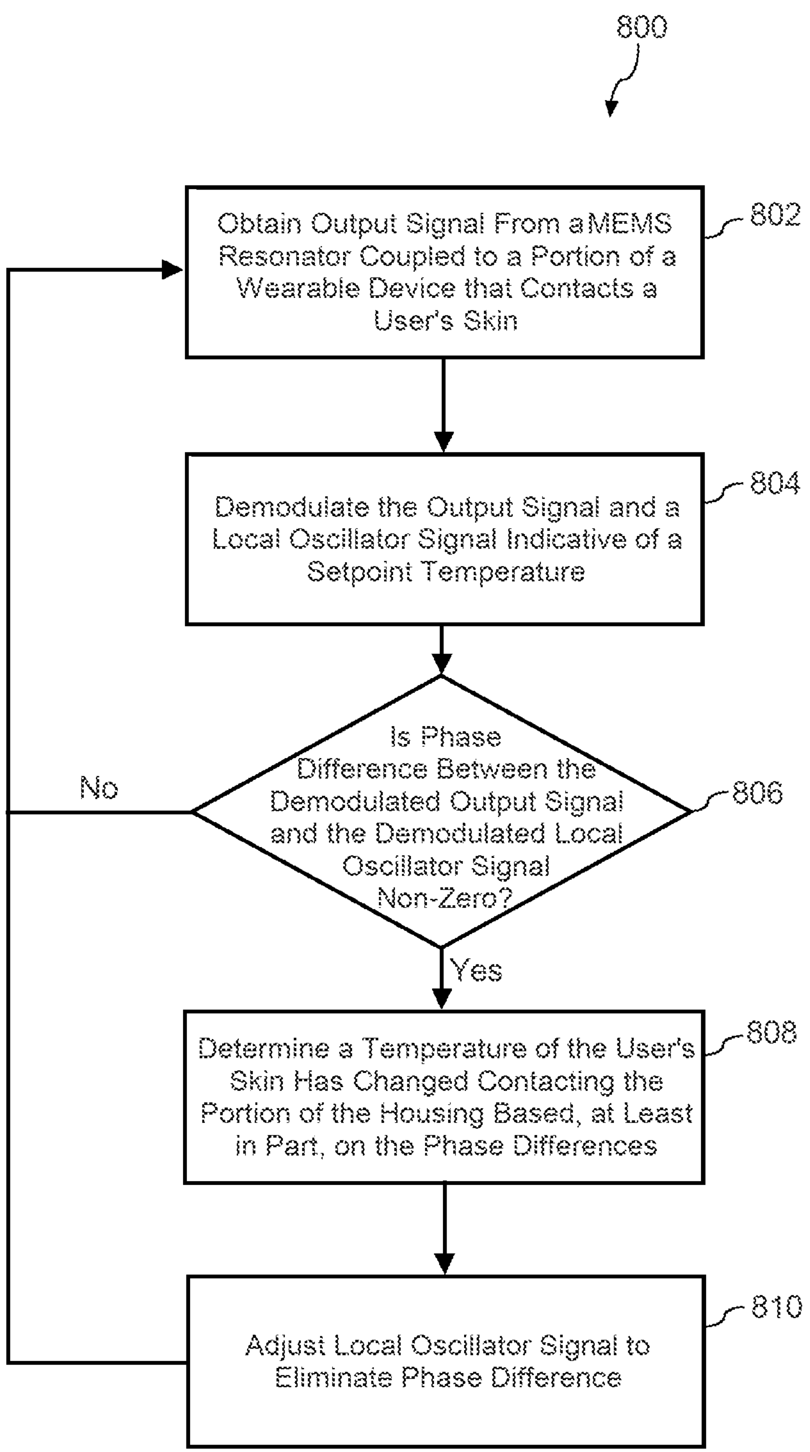
FIG. 8 depicts a flow chart diagram of an example method for determining a change to a skin temperature of a user wearing a wearable device according to some implementations of the present disclosure.

FIG. 8 depicts a flow chart diagram of an example method to perform according to example embodiments of the present disclosure. Although FIG. 8 depicts steps performed in a particular order for purposes of illustration and discussion, the methods of the present disclosure are not limited to the particularly illustrated order or arrangement. The various steps of the method 800 can be omitted, rearranged, combined, and/or adapted in various ways without deviating from the scope of the present disclosure.

At 802, the method 800 can include obtaining, at a temperature sensing circuit, an output signal (e.g., a square-wave) from the MEMS resonator that is indicative of a temperature of a portion of the wearable device that contacts a user's skin when the wearable device is worn by the user.

At 804, the method 800 can include demodulating the output signal and a local oscillator signal generated by the temperature sensing circuit and indicative of a setpoint temperature for the portion of the wearable device to determine a phase difference between a phase of the output signal and a phase of the local oscillator signal. In some implementations, demodulating the output signal and the local oscillator signal can include synchronously demodulating the output signal and the local oscillator signal.

In some implementations, demodulating the output signal and the local oscillator signal can include providing the output signal as a first input to a mixer of a demodulator of the temperature sensing circuit and providing the local oscillator signal as a second input to the mixer. The demodulator can be configured to output a first signal associated with the output signal and a second signal associated with the local oscillator signal. Additionally, demodulating the output signal and the local oscillator signal can include filtering the first signal and the second signal to generate a first filtered signal and a second filtered signal, respectively. Furthermore, in such implementations, the phase difference can be determined based, at least in part, on the first filtered signal and the second filtered signal.

At 806, the method 800 can include determining whether a phase difference between the output signal from the MEMS resonator and the local oscillator signal output by the local oscillator is non-zero. If the phase difference is non-zero, the method 800 proceeds to 808. Otherwise, the method 800 reverts to 802.

At 808, the method 800 can include determining a temperature of the skin of the user has changed based, at least in part, on the phase difference. For instance, in some implementations, the magnitude of the phase difference can be indicative of how much the temperature of the portion of the wearable device has changed from the setpoint temperature and can therefore be indicative of the change to the temperature of the user's skin. In this manner, the temperature of the user's skin can be estimated based, at least in part, on how much the temperature of the portion of the wearable device that contacts the user's skin has changed.

At 810, the method 800 can include adjusting a local oscillator signal such that the phase difference becomes zero again and the temperature sensing circuit is ready to detect another change to a temperature of the user's skin. For instance, the temperature sensing circuit can generate one or more commands associated with adjusting the local oscillator to thereby adjust the local oscillator signal as needed to eliminate the phase difference.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A wearable device comprising:

a micro-electromechanical system (MEMS) resonator configured to generate an output signal that is indicative of a temperature of a portion of the wearable device that contacts skin of a user when the wearable device is worn by the user and facilitates clocking of the wearable device; and control circuitry communicatively coupled to the MEMS resonator, wherein the control circuitry comprises a phase-locked loop circuit comprising a demodulator, a local oscillator source, and a proportional integral derivative (PID) controller, the control circuitry configured to:

demodulate, via the demodulator, the output signal and a local oscillator signal generated by the local oscillator source indicative of a setpoint temperature for the portion of the wearable device that is in contact with the user's skin when the wearable device is worn by the user;

determine a phase difference exists between a phase of the demodulated output signal and a phase of the demodulated local oscillator signal;

determine a temperature of the skin of the user has changed based, at least in part, on the phase difference being non-zero;

in response to determining the phase difference being non-zero, adjust, via the PID controller, the local oscillator signal to eliminate the phase difference; and provide the output signal generated by the MEMS resonator to one or more computing devices of the wearable device to facilitate clocking of the one or more computing devices of the wearable device.

2. The wearable device of claim 1, wherein the local oscillator source comprises a numerically controlled oscillator.

3. The wearable device of claim 1, wherein the demodulator is configured to synchronously demodulate the local oscillator signal and the output signal.

4. The wearable device of claim 1, wherein the MEMS resonator is integrally formed with the portion of the wearable device that contacts the skin of the user when the wearable device is worn by the user.

5. The wearable device of claim 1, wherein the MEMS resonator is coupled to the portion of the wearable device that contacts the skin of the user.

6. The wearable device of claim 1, wherein the portion of the wearable device is formed from a thermoelectric material.

7. A method for estimating skin temperature of a user wearing a wearable device having a housing and a microelectromechanical system (MEMS) resonator, the method comprising:

obtaining, at control circuitry of the wearable device, an output signal from the MEMS resonator, the output signal indicative of a temperature of a portion of the wearable device that contacts skin of a user when the wearable device is worn by the user and facilitates clocking of the wearable computing device, wherein the control circuitry comprises a phase-locked loop circuit comprising a demodulator, a local oscillator source, and a proportional integral derivative (PID) controller;

demodulating, at the demodulator of the control circuitry, the output signal and a local oscillator signal generated by the local oscillator source of the control circuitry and indicative of a setpoint temperature for the portion of the wearable device;

determining, at the control circuitry, a phase difference between a phase of the demodulated output signal and a phase of the demodulated local oscillator signal;

determining, at the control circuitry, a temperature of the skin of the user has changed based, at least in part, on the phase difference being non-zero;

in response to determining the phase difference being non-zero, adjusting, via the PID controller, the local oscillator signal to eliminate the phase difference; and providing, via the control circuitry, the output signal of the MEMS resonator to one or more computing devices of the wearable computing device to facilitate clocking of the one or more computing devices of the wearable device.

8. The method of claim 7, wherein demodulating the output signal comprises:

providing the output signal as a first input to a mixer of the demodulator of the control circuitry and the local oscillator signal as a second input to the mixer of the demodulator of the control circuitry to obtain a first output signal and a second output signal;

filtering the first output signal to obtain the demodulated output signal and filtering the second output signal to obtain the demodulated local oscillator signal.

9. The method of claim 7, wherein demodulating the output signal and the local oscillator signal comprises synchronously demodulating the output signal and the local oscillator signal.

10. The method of claim 7, further comprising:

determining, via the control circuitry, the temperature of the skin of the user based, at least in part, on the phase difference;

comparing, via the control circuitry, the temperature of the skin of the user to a threshold temperature;

generating, via the control circuitry, a notification in response to determining the temperature of the skin of the user is above the threshold temperature by a first predetermined amount or below the threshold temperature by a second predetermined amount.

11. The method of claim 10, wherein the notification comprises at least one of an audio notification or a visual notification.

* * * * *